US007399182B2

(12) United States Patent
Olivier

(10) Patent No.: US 7,399,182 B2
(45) Date of Patent: Jul. 15, 2008

(54) METHODS AND APPARATUS FOR DETERMINING HORIZONTAL AND VERTICAL PLANE ORIENTATION FOR CONSTRUCTION OF DENTAL PROSTHESES

(76) Inventor: Juan Olivier, 13925 Maple Hollow Cir., Draper, UT (US) 84020

(*) Notice: Subject to any disclaimer, the term of this patent is extended or adjusted under 35 U.S.C. 154(b) by 0 days.

(21) Appl. No.: 11/261,084

(22) Filed: Oct. 28, 2005

(65) Prior Publication Data
US 2006/0121409 A1 Jun. 8, 2006

Related U.S. Application Data

(60) Provisional application No. 60/623,647, filed on Oct. 29, 2004.

(51) Int. Cl.
A61C 19/04 (2006.01)
A61C 11/00 (2006.01)
(52) U.S. Cl. .......................................... 433/73; 433/54
(58) Field of Classification Search ............. 433/54–57, 433/63, 68, 71–75
See application file for complete search history.

(56) References Cited

U.S. PATENT DOCUMENTS

| 90,705 | A | | 6/1869 | Von Bonhorst | |
| 1,589,973 | A | * | 6/1926 | Landa | 33/514 |
| 1,649,664 | A | | 11/1927 | Carter | |
| 1,662,670 | A | * | 3/1928 | Harter | 33/514 |
| 1,679,748 | A | * | 8/1928 | Stratton | 425/2 |
| 1,786,915 | A | | 12/1930 | McLean | |
| 1,944,801 | A | | 1/1934 | Gulick | |
| 2,334,643 | A | * | 11/1943 | Moore | 433/56 |
| 2,695,451 | A | | 11/1954 | Hipp | |
| 2,727,307 | A | | 12/1955 | Clark | |
| 2,758,375 | A | | 8/1956 | Badovinac et al. | |
| 2,908,975 | A | | 10/1959 | Uessem | |
| 3,024,534 | A | * | 3/1962 | Wilkinson | 433/73 |
| 3,084,438 | A | * | 4/1963 | Goodfriend | 433/73 |
| 3,106,779 | A | | 10/1963 | Benjamin | |
| 3,200,497 | A | * | 8/1965 | Goodfriend | 433/44 |
| 3,557,455 | A | * | 1/1971 | Stuart | 433/68 |
| 3,724,099 | A | * | 4/1973 | Stuart | 433/68 |
| 3,936,937 | A | * | 2/1976 | Gordon | 433/77 |
| 4,286,947 | A | | 9/1981 | Daiberl | |
| RE31,426 | E | | 10/1983 | Daiberl | |
| 4,634,377 | A | | 1/1987 | Behrend | |
| 4,639,220 | A | | 1/1987 | Nara et al. | |
| 4,823,476 | A | | 4/1989 | Curtin | |
| 4,843,720 | A | | 7/1989 | Kim | |

(Continued)

OTHER PUBLICATIONS

"Symmetry Facial Plane Relator." Http://www.clinicianschoice.com/c/c_symm.htm Jun. 28, 2004, pp. 1-10.

Primary Examiner—Cary E. O'Connor
(74) Attorney, Agent, or Firm—Morriss O'Bryant Compagni

(57) ABSTRACT

Methods and systems for establishing dental bite planes in relation to the relative vertical and horizontal planes of a patient's face and head. A U-shaped bite fork, which can be held by the patient's teeth or gums, may be attached to a connection system that attaches to adjustable orientation rods that may be aligned to the vertical and horizontal planes of the patient's face and head. Once the orientation rods are correctly adjusted, the orientation rods may be may be locked into place to preserve the orientation of the patient's bite plane relative to the facial reference planes.

19 Claims, 7 Drawing Sheets

U.S. PATENT DOCUMENTS

| | | |
|---|---|---|
| 4,997,368 A | 3/1991 | Mayer et al. |
| 5,176,515 A * | 1/1993 | Andrews ..................... 433/24 |
| 5,685,084 A | 11/1997 | Demers |
| 5,810,586 A | 9/1998 | Fjelstad |
| 5,857,853 A | 1/1999 | van Nifterick et al. |
| 5,971,756 A | 10/1999 | Fjelstad |
| 6,048,322 A | 4/2000 | Kushida |
| 6,109,917 A * | 8/2000 | Lee et al. ..................... 433/73 |
| 6,213,959 B1 | 4/2001 | Kushida |
| 6,413,085 B1 | 7/2002 | Lee |
| 6,582,931 B1 * | 6/2003 | Kois et al. ..................... 435/56 |
| 7,156,658 B2 | 1/2007 | Shoup |
| 2004/0177852 A1 | 9/2004 | Abramson |
| 2006/0040232 A1 | 2/2006 | Shoup |
| 2006/0147872 A1 | 7/2006 | Andreiko |

* cited by examiner

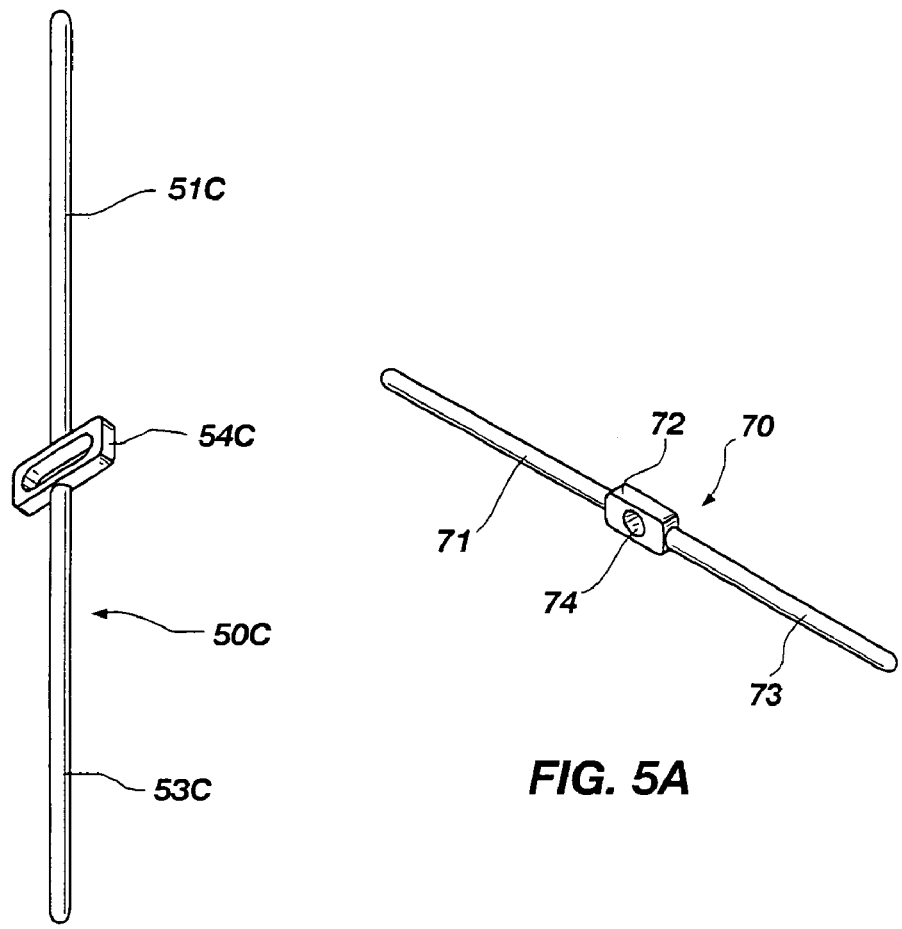
FIG. 4C
FIG. 5A
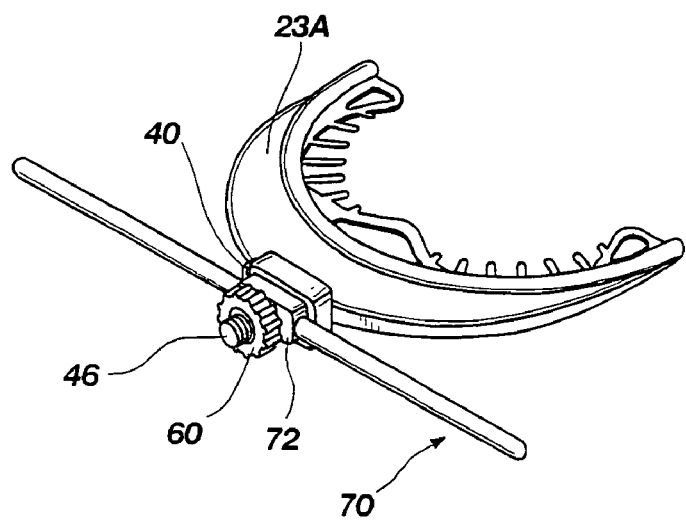
FIG. 5B

METHODS AND APPARATUS FOR DETERMINING HORIZONTAL AND VERTICAL PLANE ORIENTATION FOR CONSTRUCTION OF DENTAL PROSTHESES

CROSS-REFERENCE TO RELATED APPLICATION

This application claims the benefit of U.S. Provisional Application No. 60/623,647, filed Oct. 29, 2004, which is incorporated herein by reference in its entirety.

TECHNICAL FIELD

The present invention relates generally to methods and apparatus for determining a bite plane orientation. More particularly, the present invention relates to methods and apparatus for easily and accurately establishing and recording a patient's bite plane in relation to the relative horizontal and vertical alignment of the patient's face and head. The bite plane orientation may then be used in the fabrication of dental restorations and prosthetics.

BACKGROUND

While sitting or standing in a natural position, a patient's teeth should have an orientation that appears well centered and leveled in reference to the patient's facial features. Horizontal and vertical reference planes must be considered to create an attractive and natural looking set of teeth that allow for proper mastication and occlusion. If a patient's face were perfectly symmetrical, the mid-line between the central incisors should be parallel and centered with the sagittal mid-line. Additionally, the patient's maxillary anterior incisal line, also known as the "bite plane" or "bite register", should be parallel with the inter-pupillary eye line, a horizontal reference plane, and perpendicular with the sagittal mid-plane. However, very few individuals have perfect facial symmetry and dental orientation.

Often, bite impressions of the teeth necessary for dental restorations, prosthodontics, orthodontics or other procedures are taken without information regarding the orientation of the teeth or bite plane relative to the features of the face and head. Without the proper orientation, the resulting dental casts can lead to the creation of dental restorations with improper occlusion of the patient's teeth and numerous aesthetic problems including an unnatural bite plane or a slanted maxillary mid-line and gum line.

As patients became increasingly concerned with proper function, appearance and aesthetics of their dental work, methods were developed to provide an accurate orientation of the bite plane. For example U.S. Pat. No. 2,695,451 is directed to a device for determining the proper alignment of upper and lower jaw impressions, U.S. Pat. No. 2,908,975 is directed to a device for orienting impressions taken for making dental plates, bridges and other dental work, U.S. Pat. No. 3,200,497 is directed to a method of reproducing the spatial orientation of bite impressions for the production of dental replacements and dentures, U.S. Pat. No. 4,639,220 is directed to an apparatus for measuring the three-dimensional position of upper and lower bite impressions for fabrication of dental prosthesis, U.S. Pat. No. 5,810,586 is directed to an apparatus to determine the placement and relative position of upper and lower dentures, U.S. Pat. No. 6,109,917 is directed to a dental apparatus for determining a patient specific reference plane for aesthetic positioning of dental casts, and, finally, U.S. Pat. No. 6,413,085 is directed to a system for configuring and aligning anterior maxillary teeth. The disclosure of each of these references in incorporated in its entirety herein. None of these devices allow a rapid determination of the patient's bite plane with a rigid apparatus that is easily adjustable for determining the horizontal and vertical planes of a patient's face, and, can be locked to record a correct position of the determination.

It would be desirable to provide an apparatus and method for easily and accurately determining the bite plane of a patient in relation to the horizontal and vertical symmetry of the patient's face and head. Such apparatus and methods for determining bite plane orientation of a patient that easily accommodates variance in patient symmetry and anatomy would be further desirable.

SUMMARY

The present invention is directed to systems and methods for establishing a patient's bite plane in relation to the vertical and horizontal reference planes of the patient's face and head. The apparatus may include a generally U-shaped bite fork sized to fit in the patient's mouth, which may be held in place by the patient's teeth or gums. The bite fork may be attached to a connection system and one or more orientation rods. The connection system may be configured to allow alignment of vertical and horizontal orientation rods with the vertical, horizontal and/or frontal planes of the patient's face and head. Once an orientation rod is correctly adjusted, the connection system of the apparatus may be locked into place to preserve the orientation of the patient's bite plane relative to the facial reference planes. The apparatus may then be used to produce dental prostheses with the proper alignment relative to a patient's bite plane.

The method may include establishing the orientation of a dental bite plane in relation to the facial planes of symmetry of a patient by placing a bite fork into the patient's mouth while engaging the teeth (with the bite fork, or by placing the bite fork into a separate bite impression material), such that a connection housing extends from the bite fork and out of the mouth of the patient. A vertical orientation rod and a horizontal orientation rod may then be connected to the connection housing by a connection plate, either together or separately as desired by the specific embodiment. The vertical orientation rod may be adjusted until it is substantially parallel with the sagittal mid-line of the patient's head. In some embodiments, the vertical orientation rod may also be adjusted to be substantially parallel to the frontal plane of the patient's head. Similarly, the horizontal orientation rod is adjusted until it is substantially parallel with a horizontal reference plane of the patient's interpupillary line. The orientation rods may then be locked in place with respect to the connection plate in order to record the desired planes. The orientation rods may be locked into place concurrently or independently. For example, the vertical orientation rod may be locked into place and removed from the connection housing plate followed by positioning and locking the horizontal orientation rod into place. A bite impression taken while the orientation planes are recorded may later be properly oriented, relative to the planes of the patient's head, by referring to the record made by the orientation rods of the bite fork.

DESCRIPTION OF THE DRAWINGS

It will be appreciated by those of ordinary skill in the art that the various drawings are for illustrative purposes only. The nature of the present invention, as well as other embodiments of the present invention, may be more clearly understood by reference to the following detailed description of the invention, to the appended claims, and to the several drawings.

FIG. 4C is a perspective view of a second illustrative embodiment of a vertical orientation rod that may be used in a system in accordance with the present invention.

FIG. 5A is a perspective view of an illustrative embodiment of a horizontal orientation rod that may be used in a system in accordance with the present invention.

FIG. 5B is a perspective view of the horizontal orientation rod of FIG. 5A in a system of the present invention including the bite fork of FIG. 1.

DETAILED DESCRIPTION

The present invention relates to systems and methods for aligning and recording facial planes with respect to a dental bite plane. It will be appreciated by those skilled in the art that the embodiments herein described, while illustrating certain embodiments, are not intended to so limit the invention or the scope of the appended claims. Those skilled in the art will also understand that various combinations or modifications of the embodiments presented herein can be made without departing from the scope of the invention. All such alternate embodiments are within the scope of the present invention.

Figure 1A:
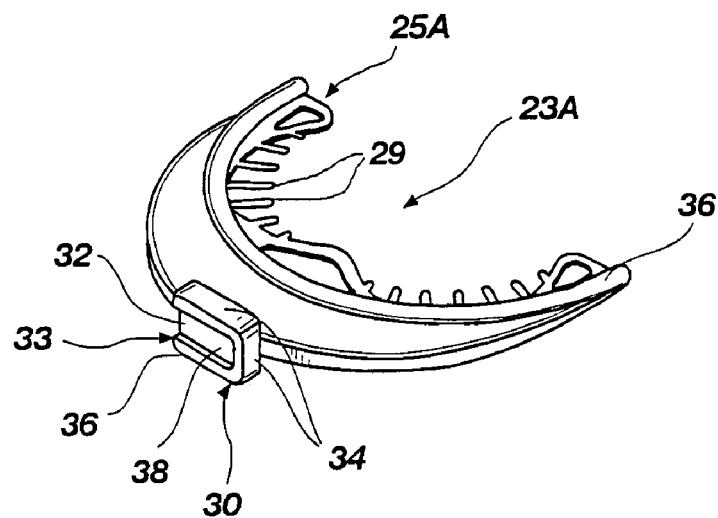
FIG. 1A is a perspective view of one illustrative embodiment of a bite fork that may be used in a system in accordance with the present invention.

Turning to FIG. 1A, an embodiment of a bite fork 23A for use with an orientation system 20 is depicted. The bite fork 23A may be sized and configured to fit in the patient's mouth and may be held in place by the upper and lower teeth or gums of the patient. The bite fork 23A may be sized and configured with a substantially flat and U-shaped bite plate generally indicated at 25A rimmed by a vertical ridge 26 which may facilitate the positioning of the bite fork 23A in the patient's mouth, although it will be appreciated that in some embodiments, the bite fork 23 may also be substantially flat without a vertical component. In some embodiments, the substantially flat bite plate 25 may appear as an array of engagement tabs 29 configured to engage with a raw impression material placed on the patient's teeth. As a bite impression is taken, the bite fork 23A may be held in place until the bite impression material is cured and remain therein.

Figure 1B:
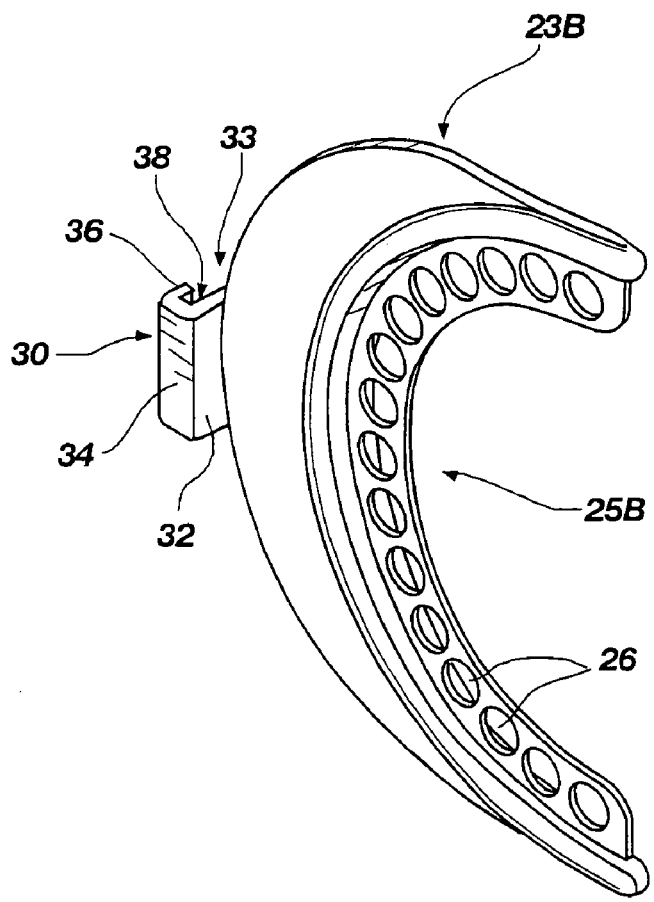
FIG. 1B is a perspective view of a second illustrative embodiment of a bite fork that may be used in a system in accordance with the present invention.

Turning to FIG. 1B, a second illustrative embodiment of a U-shaped bite fork 23B is depicted. The generally flat bite plane, 25B lacks engagement tabs, instead appearing as a flat biting surface, with a number of openings 26 passing therethrough. Although the openings 26 are depicted as circular, the shape of the opening may vary as desired, so long as uncured bite impression material may pass therethrough to allow the bite fork 23B to become embedded into the cured impression material.

Other embodiments of dental bite forks 23 may be used as appropriate for the present invention. For example, embodiments where a mesh lattice is formed in place of the bite plate 25 are contemplated. The bite fork 23 may be of various sizes to accommodate different mouth sizes in small children, adolescents, and adults. Similar to the openings 26, a mesh lattice may serve to engage a raw bite impression material by allowing it to flow between the holes of the mesh and to be held in the patient's mouth until the bite impression material has cured, thus anchoring the bite impression material to the bite fork 23. A mesh lattice may be molded and integrated with the bite fork 23 or may be inserted separately. A bite fork 23 may be made of any suitable material, including rigid materials such as stainless steel, other metals, or plastics. If desired, the bite fork 23 may include a large bite plane that is configured to make bite impressions of the patient's teeth or gums.

At the front of the bite fork 23A or 23B is a connection member, such as the receiving bracket 30. The connection member is configured to removably connect with a connection element (shown in FIG. 2). As depicted, the receiving bracket 30 includes a planar base 32, the major plane of which is perpendicular to the bite plane 25A. The planar base 32 is partially surrounded by sidewalls 34, which connect to a top rim 36, which is parallel to the planar base 32. A connection space 38 is formed by perimeter of the planar base 32, the sidewalls 34 and the top rim 36. The planar base 32 is exposed through a central opening 35. Access into the connection space 38 is provided by at least one gap in the sidewalls 34 and top rim 36, such as the insertion entrance 33.

Figure 2:
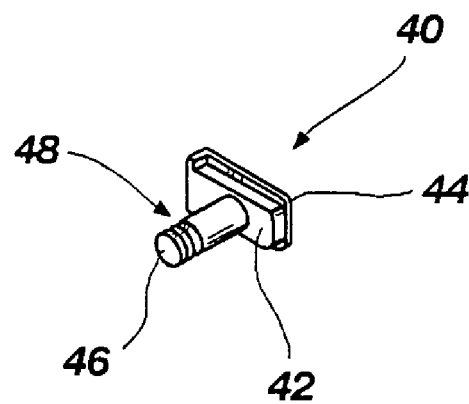
FIG. 2 is a perspective view of an illustrative embodiment of a connection element that may be used in a system in accordance with the present invention.
Figure 3:
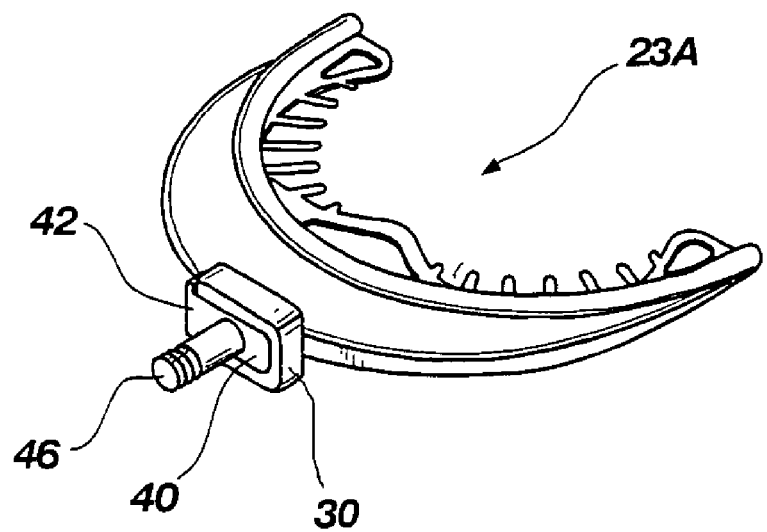
FIG. 3 is a perspective view of the connection element of FIG. 2 connected to the bite fork of FIG. 1.

Turning to FIGS. 2 and 3 a connection element 40 is depicted. Connection element 40 includes a generally rectangular planar base 42, which has a shaft 46 protruding from a front surface thereof. The shaft 46 may be configured for interaction with a locking element, as by threads 48. A ridge 44 may be present at the rear surface of the base 42. Ridge 44 fits closely in connection space 38, upon insertion of the connection element 40 into receiving bracket 30, as depicted in FIG. 2A. Ridge 44 may terminate at stop 47, to ensure that connection element 40 may only be inserted into receiving bracket 30 in one conformation. It will be appreciated that alternative embodiments lacking a ridge 44, where the entire side of base 42 resides within the connection space 38 upon insertion, are contemplated within the scope of the present invention. It will be further appreciated that threads 48 may be disposed along the entire length of the shaft 46 or along a distal portion of the shaft 46, as required for retention of an orientation rod, as discussed further herein. Embodiments where shaft 46 is not threaded, but interacts with a retaining knob that either threads the shaft upon application or fits tightly enough thereon to retain an orientation rod in position without threads may be used.

Figure 4A:
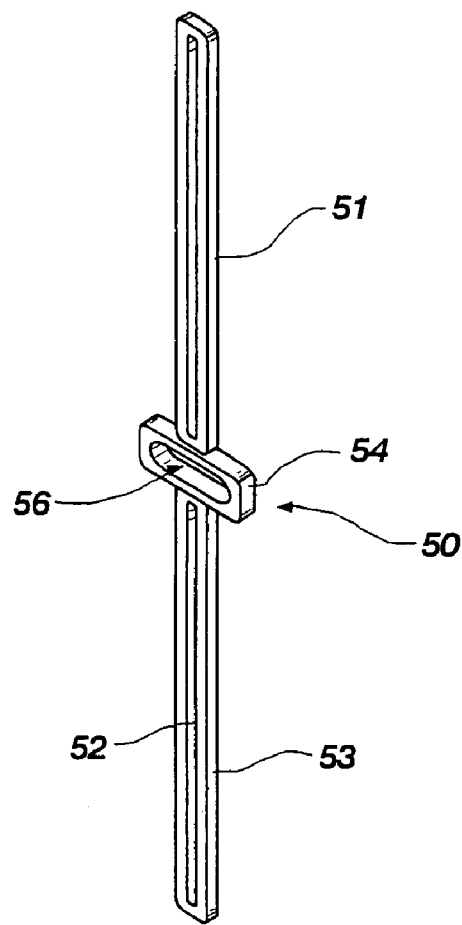
FIG. 4A is a perspective view of an illustrative embodiment of a vertical orientation rod that may be used in a system in accordance with the present invention.
Figure 4B:
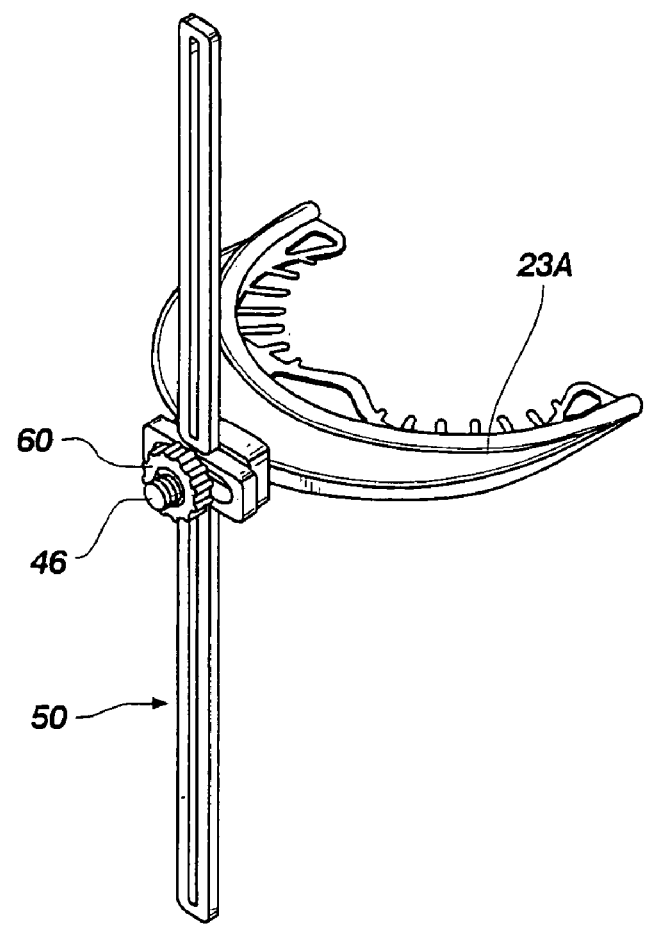
FIG. 4B is a perspective view of the vertical orientation rod of FIG. 4A in a system of the present invention including the bite fork of FIG. 1.

FIGS. 4A and 4B depict a vertical orientation rod 50 that may be used with a system of the present invention for alignment with the sagittal mid-line reference plane of a patient. As depicted, vertical orientation rod 50 includes an upper shaft 51 and a lower shaft 53 extending opposite each other from an adjustment fitting 54. Adjustment fitting 54 includes an adjustment slot 56. For use, the vertical orientation rod 50 is attached to connection element 40 by placing the adjustment fitting 54 over a shaft 46, such that the distal end of shaft 46 protrudes through the adjustment slot 56. The vertical orientation rod 50 may then be aligned with a patient's sagittal mid-line reference plane by tilting the vertical orientation rod 50 along its long axis around shaft 46 and by laterally adjusting the vertical orientation rod 50 by lateral movement of the adjustment slot 56 in relation to shaft 46. Upon correct alignment, the vertical orientation rod may then be held in position by tightening a nut or knob 60 on shaft 46.

The upper shaft 51 and lower shaft 53 of a vertical orientation rod 50 may contain a central visualization slot 52 to allow a user to better visualize the patient's sagittal mid-line reference plane for alignment. However, a vertical orientation rod, such as that depicted in FIG. 4C, where the upper and lower shafts 51C and 53C are single rods extending from the alignment fitting 54C may be used, where desired.

Turning to FIGS. 5A and 5B, a horizontal orientation rod 70 in accordance with the principles of the present invention is depicted. A central attachment fitting 72 includes an alignment opening 74 therein. Alignment shafts 71 and 73 extend out from opposite sides of the attachment fitting 72. For use, the horizontal orientation rod 70 is attached to a connection element 40 by placing the alignment fitting 72 over a shaft 46, such that the distal end of shaft 46 protrudes through the alignment opening 74. The horizontal orientation rod 70 may then be aligned with a patient's horizontal reference plane by tilting the orientation rod along its long axis around shaft 46. Upon correct alignment, the horizontal orientation rod 70 may then be held in position by tightening a nut or knob 60 on shaft 46.

Figure 6:
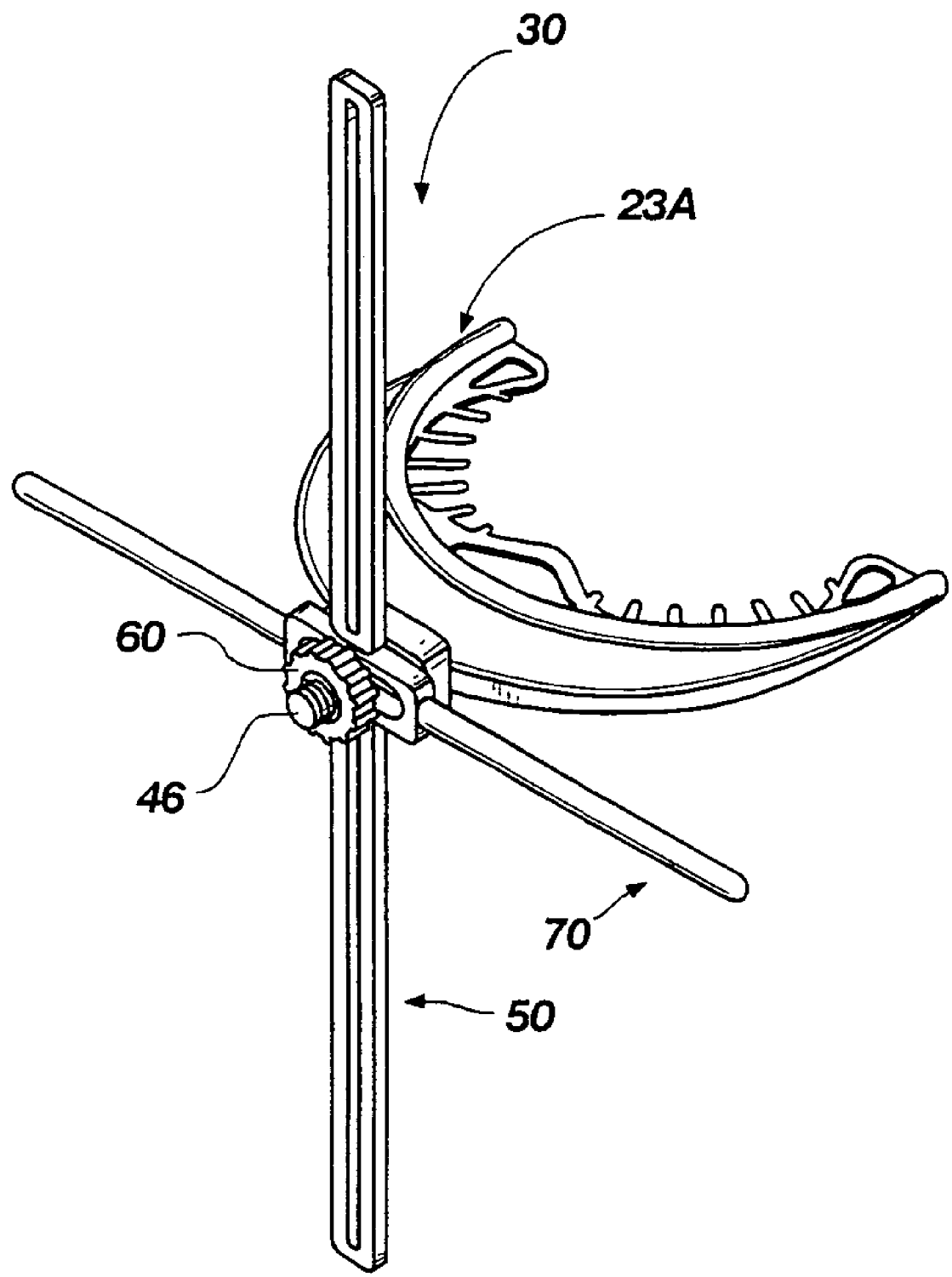
FIG. 6 is a perspective view of another system in accordance with the present invention including the vertical orientation rod of FIG. 4A and the horizontal orientation rod of FIG. 5A and the bite fork of FIG. 1.

FIG. 6 depicts an embodiment of a system 20 in accordance with the present invention, where the vertical orientation rod 50 and horizontal orientation rod 70 are placed on the same shaft 46 of a connection element 40 attached to a bite fork 23. With such an embodiment, each rod may be aligned to its respective reference plane, and the knob 60 tightened to retain both rods in position.

Figure 7:
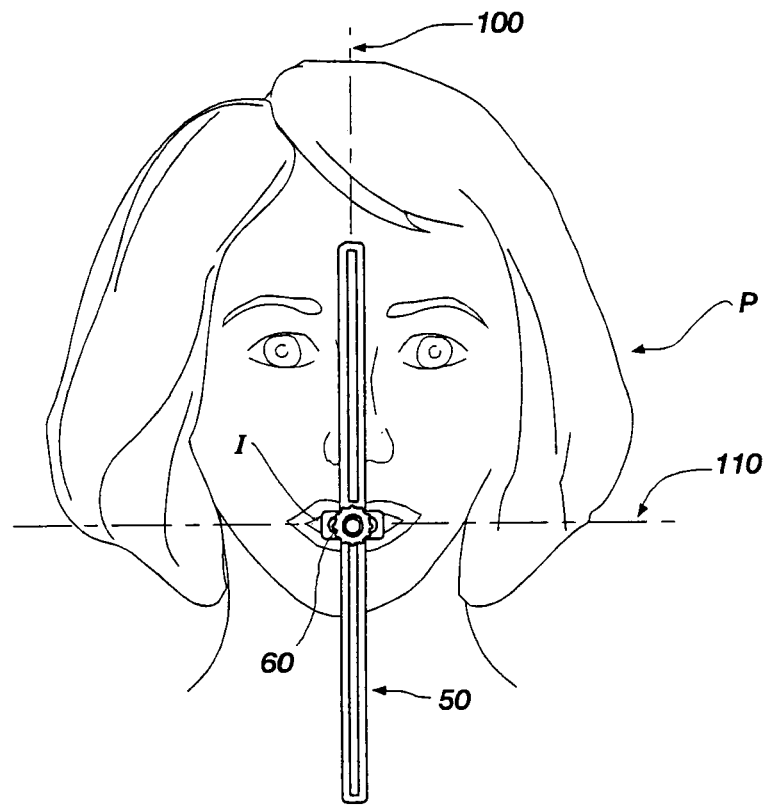
FIG. 7 is a front view representing a system of the present invention in use with a patient to determine relative dental planes.
Figure 8:
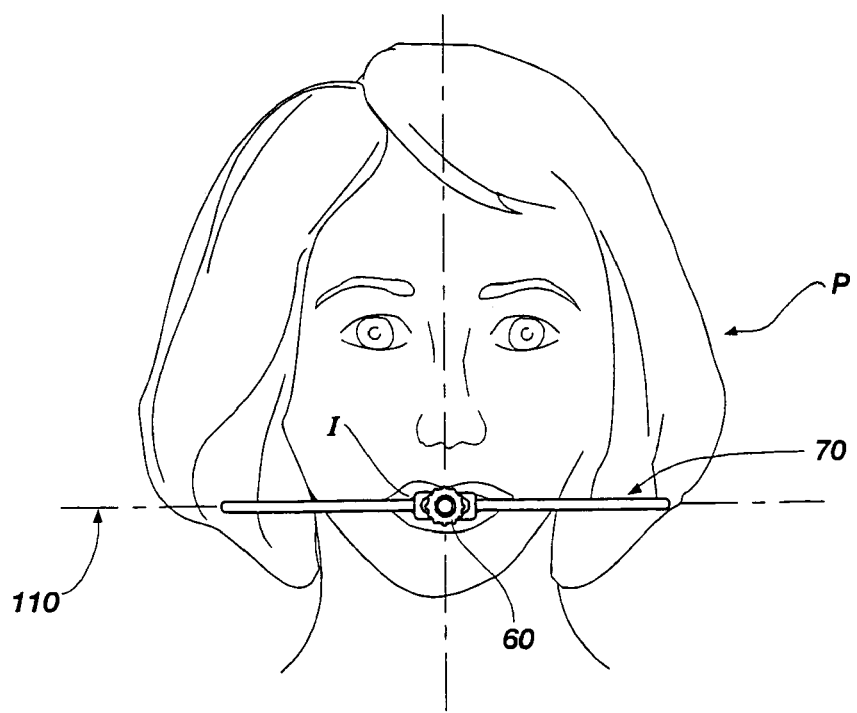
FIG. 8 is a front view representing systems of the present invention in use with a patient to determine relative dental planes.

The present invention includes methods of establishing bite planes in relation to anatomical planes of symmetry and orientation. Referring to FIGS. 7 and 8, the sagittal mid-line reference plane or line 100 lies in the anterior-posterior direction. The sagittal mid-line reference plane 100 bisects a patient's body into theoretically symmetrical right and left halves. The horizontal reference plane 110 is a general reference plane established by having the patient sit upright in a natural fashion and then envisioning a plane that generally describes the apparent level horizontal plane of the patient's head. The horizontal reference plane 110 is generally perpendicular to the sagittal mid-line reference plane 100. The frontal reference plane 120 is another general plane established by having the patient P sit straight upright in a natural fashion and then envisioning a plane running across the face that generally describes the overall plane of the patient's face. The frontal reference plane 120 is generally perpendicular to the sagittal mid-line reference plane 100 and generally perpendicular to the horizontal reference plane 110. It will be appreciated that the exact angle of each of these planes and lines and their relationship to one another, will vary from individual to individual.

Figure 7A:
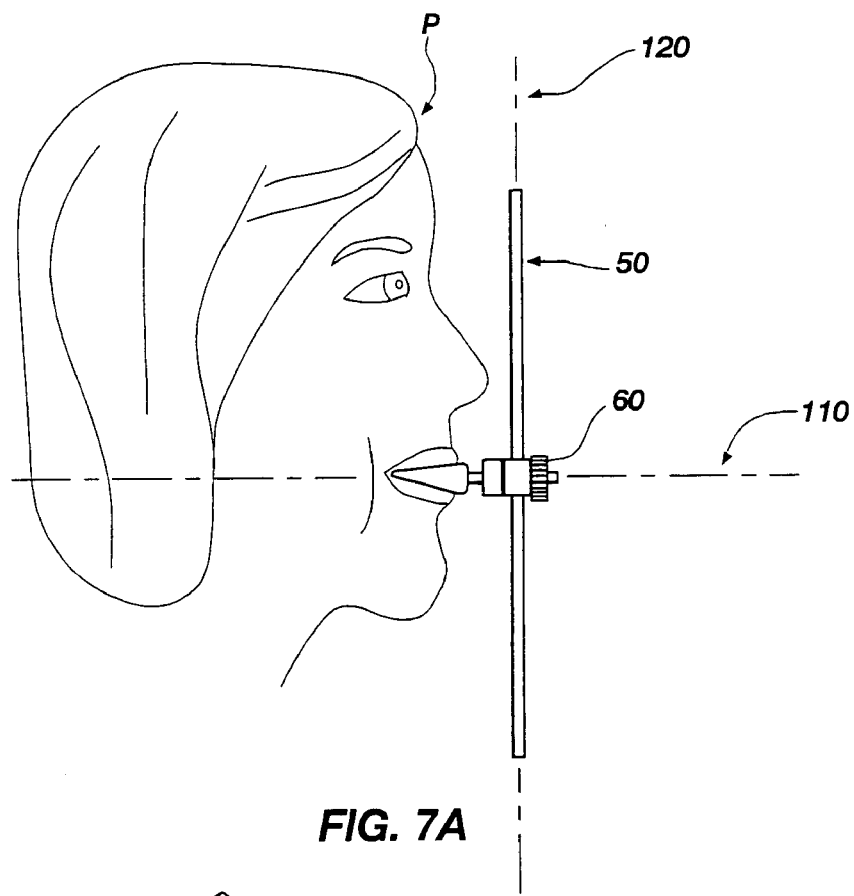
FIG. 7A is a side view of FIG. 7.

Knowing the orientation of the bite plane or bite register relative to the patient's face and head helps to create dental restorations and prostheses that are more functional, comfortable and attractive. As shown in FIGS. 7, 7A and 8, a patient holds a bite fork 23 in the mouth, preferably between the teeth. Where the bite fork is configured for embedding in bite impression material, this may occur after uncured material is placed over the patient's teeth with the bite fork 23 embedded in the bite impression material 1. A connection element 40 is placed in connection bracket. At least one orientation rod is placed on the shaft 46. FIGS. 7 and 7A depict a system with a vertical orientation rod 50 in place. The vertical orientation rod is adjusted by rotation and lateral motion to determine the sagittal mid-line reference plane or line 100. upon adjustment, the vertical orientation rod may be accurate dead center on the contact point of the middle of the center incisors with the central visualization slot 52. The vertical orientation rod 50 may then be locked in place with knob 60 to record the sagittal mid-line reference plane or line. Connection element 40 may then be removed from the bite fork 23 while retaining the recordation of the angular relationship thereto. In some embodiments, the vertical orientation rod 50 may be tipped forwards or backwards along its long axis to record a frontal plane of the patient P.

Similarly, as depicted in FIG. 8, a second connection element 40 may be placed in connection bracket and a horizontal orientation rod 70 placed thereon. The horizontal orientation rod may then be adjusted by rotation to determine the horizontal reference plane or line 110. The horizontal orientation rod 70 may then be locked in place with knob 60 to record the horizontal reference plane or line. Connection element 40 may then be removed from the bite fork 23 while retaining the recordation of the angular relationship thereto. As most individuals vary from having perfectly perpendicular and perfectly proportioned features (for example the lips may be slightly crooked on the patient's face), the recordation of such lines allows for the creation of dental prosthetics that appear more attractive on the patient. It will be appreciated that in some embodiments the horizontal orientation rod 70 and vertical orientation rod 50 may be positioned and locked at the same time, if desired by the dental practitioner.

Each separated connection element 40 together with the attached orientation rod(s) and knob and the bite fork 23 may then be provided to the dental prosthetic manufacturer such the record of the planes may be used in the creation of the dental prosthetics. With the orientation rods and the connection element 40 detached, the entire system will fit in a smaller mailing package and can be reassembled upon arrival at the dental laboratory. Furthermore, removal of the orientation rods before shipment may help eliminate bending and damage during transport while ensuring that the dental lab receives an accurate bite plane orientation. For embodiments where the connection element 40 is not removable, the entire system may be provided, which may include providing the apparatus in hardened bite impression material. Where appropriate, the bite fork 23 may be provided in the bite impression, or may be provided separately.

Figure 9:
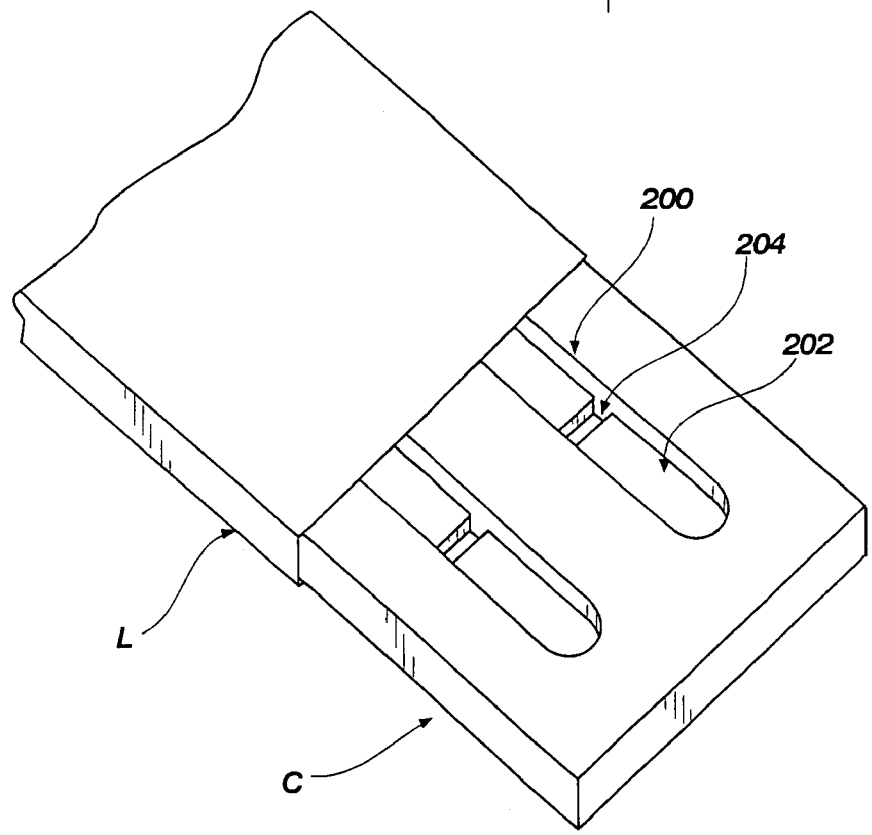
FIG. 9 is a perspective view of an illustrative embodiment of a package for a system of the present invention.

A system in accordance with the present invention may be provided to a dental practitioner in the form of a kit for determining anatomical facial planes. The kit may include at least one bite fork in accordance with the present invention, multiple connection elements and retaining structures and at least one vertical orientation rod and at least one horizontal orientation rod. The kit may include a package that is configured for retaining the orientation bars and connection elements in locked position. For example, the container C, as shown in FIG. 9, could include a compartment 200 configured for retaining an orientation bar and connection element, such as a channel 202 for holding the orientation bar and an indentation 204 within the channel 202 for holding the connection element. Multiple compartments could be included as desired. Additionally, for embodiments where both orientation bars are used in with one connection element, a generally X-shaped or cross-shaped channel may be used with an indentation placed at a center point. A cover, such as a box L, may be included. Such a package may then be used for shipping the system to a dental laboratory. The package may serve as the packaging for the kit prior to use or may be included as a smaller package with the kit.

The present invention may be embodied in other specific forms without departing from its spirit or essential characteristics. The described embodiments are to be considered in all respects only as illustrative and not restrictive

What is claimed is:

1. A system for establishing the orientation of a dental bite plane, comprising:
   a bite fork configured to be held in a patient's mouth;
   a connection fitting attached to the bite fork;
   at least one removable connection plate configured to be attached to the connection fitting, the at least one removable connection plate comprising a shaft extending from a base;
   at least one orientation rod configured to adjustably attach to the removable connection plate. such that the at least one orientation rod may be rotatably tilted with respect to the removable connection plate; and
   at least one retainer configured to attach to the removable connection plate and retain the at least one orientation rod in an adjusted position locking the at least one orientation rod in position and retaining such position upon removal of the removable connection plate from the connection fitting.

2. The system of claim 1, wherein the bite fork is configured to be held between the patient's upper and lower teeth or gums.

3. The system of claim 1, wherein the bite fork includes at least one structure for engagement with a bite impression material.

4. The system of claim 1, wherein the at least one orientation rod is configured to adjustably attach to the connection plate by insertion of the shaft through an opening in the at least one orientation rod, such that the at least one orientation rod may be tilted by rotation around the shaft.

5. The system of claim 4, wherein the opening in the at least one orientation rod comprises a slot for lateral adjustment of the orientation rod with respect to the connection plate.

6. The system of claim 1, wherein the at least one retainer comprises a nut for rotatable attachment to the shaft.

7. The system of claim 1 wherein the at least one orientation rod comprises a vertical orientation rod and a horizontal orientation rod.

8. The system of claim 1, wherein the bite fork is formed of a material selected from the group consisting of plastic, stainless steel, metal, metal alloy, ceramic, wood, carbon fiber, or any combination thereof.

9. A system for establishing the orientation of a dental bite plane, comprising:
   a bite fork configured to be held in a patient's mouth;
   a connection fitting attached to the bite fork;
   at least one removable connection plate configured to be attached to the connection fitting;
   at least one orientation rod configured to adjustably attach to the removable connection plate, such that the at least one orientation rod may be rotatably tilted with respect to the removable connection plate, the at least one orientation rod comprising a central slot for visualization of the facial plane therethrough; and
   at least one retainer configured to attach to the removable connection plate and retain the at least one orientation rod in an adjusted position locking the at least one orientation rod in position and retaining such position upon removal of the removable connection plate from the connection fitting.

10. The system of claim 9, wherein the bite fork is configured to be held between the patient's upper and lower teeth or gums.

11. The system of claim 9, wherein the bite fork includes at least one structure for engagement with a bite impression material.

12. The system of claim 9, wherein the at least one orientation rod comprises a vertical orientation rod and a horizontal orientation rod.

13. The system of claim 9, wherein the bite fork is formed of a material selected from the group consisting of plastic, stainless steel, metal, metal alloy, ceramic, wood, carbon fiber, or any combination thereof.

14. A The method of establishing the orientation of a dental bite plane in relation to a facial plane of symmetry, comprising:
   placing a bite fork in a patient's mouth;
   connecting an orientation rod to a connection housing on the bite fork by connecting the orientation rod to a removable plate inserted in the connection housing;
   rotating the orientation rod with respect to the connection housing until it is substantially parallel with a facial plane of the patient's head comprising rotating the orientation rod around a shaft disposed on the removable plate;
   locking the orientation rod in position to record the reference plane of the patient's head; and
   removing the removable plate from the connection housing with the orientation rod locked in place thereto.

15. The method according to claim 14, wherein rotating the orientation rod with respect to the connection housing until it is substantially parallel with a facial plane of the patient's head further comprises laterally moving the orientation rod with respect to a shaft disposed on the removable plate, where the shaft protrudes through a slot in the at least one orientation rod.

16. The method according to claim 14, wherein locking the orientation rod in position to record the reference plane of the patient's head comprises tightening a nut on the shaft disposed on the removable plate.

17. The method according to claim 14, wherein rotating the orientation rod with respect to the connection housing until it is substantially parallel with a facial plane of the patient's head comprises adjusting the orientation rod until it is substantially parallel to the sagittal mid-line, the horizontal reference plane, or the frontal plane of the patient's head.

18. A for recording the planes of a patient's head with respect to a bite impression, the kit comprising:
   a bite fork, with an attachment fitting disposed at a front end thereof;
   at least two removable connection plates, each removable connection plate configured for insertion into the attachment fitting;
   at least two orientation rods; each orientation rod configured to adjustably attach to a removable connection plate, such that the at least one orientation rod may be rotatably tilted with respect to that removable connection plate; and at least one retainer configured to attach to a connection plate and retain at least one orientation rod in an adjusted position locking the at least one orientation rod in position and retaining such position upon removal of the removable connection plate from the attachment fitting.

19. The kit of claim 18, further comprising a container configured for retaining an orientation bar with a connection element attached thereto.

* * * * *